(12) United States Patent
Khorsandi

(10) Patent No.: US 10,376,007 B2
(45) Date of Patent: Aug. 13, 2019

(54) STABILIZING BELT

(71) Applicant: Grip-n-Ride, LLC, Los Angeles, CA (US)

(72) Inventor: Jack Khorsandi, Los Angeles, CA (US)

(73) Assignee: GRIP-N-RIDE, LLC, Los Angeles, CA (US)

( * ) Notice: Subject to any disclaimer, the term of this patent is extended or adjusted under 35 U.S.C. 154(b) by 915 days.

(21) Appl. No.: 14/880,950

(22) Filed: Oct. 12, 2015

(65) Prior Publication Data

US 2016/0029726 A1 Feb. 4, 2016

Related U.S. Application Data

(63) Continuation-in-part of application No. 14/296,305, filed on Jun. 4, 2014, now abandoned, which is a continuation-in-part of application No. 14/144,401, filed on Dec. 30, 2013, now Pat. No. 9,474,314, which is a continuation-in-part of application No. 13/540,502, filed on Jul. 2, 2012, now Pat. No. 8,617,092, which is a continuation of application No. 12/854,823, filed on Aug. 11, 2010, now Pat. No. 8,211,043, which is a continuation-in-part of
(Continued)

(51) Int. Cl.
*A61F 5/03* (2006.01)
*A41F 9/00* (2006.01)
*A61F 5/00* (2006.01)
*A61F 5/02* (2006.01)

(52) U.S. Cl.
CPC ............... *A41F 9/005* (2013.01); *A61F 5/00* (2013.01); *A61F 5/02* (2013.01); *A61F 5/028* (2013.01)

(58) Field of Classification Search
CPC .......... A61F 5/0009; A61F 5/02; A61F 5/024; A61F 5/026; A61F 5/028; A41F 9/005; A61G 7/10; A61G 7/1038; A61G 7/1023; A44B 11/2503; A41B 11/2553; A45F 3/14; A45F 2003/144; B62J 2027/005; A62B 35/00
USPC ...................................................... 128/869
See application file for complete search history.

(56) References Cited

U.S. PATENT DOCUMENTS 227,708 A 5/1880 Williard
2,810,511 A * 10/1957 Cantor .................. B65D 27/24
229/77
(Continued)

FOREIGN PATENT DOCUMENTS

DE 101 22 725 A1 5/2002
GB 2 180 293 A 9/1986
WO WO 92/13469 8/1992

*Primary Examiner* — Kari K Rodriquez
*Assistant Examiner* — Camtu T Nguyen
(74) *Attorney, Agent, or Firm* — Cislo & Thomas, LLP

(57) ABSTRACT

A stabilizing belt for use by a person in need of assisted mobility or in recreation, the stabilizing belt comprising a base, a belt to secure the base to a wearer, and at least one handle attached to the base. The base may be uniquely contoured to provide support and comfort for the wearer. A harness system may be provided for added security and stability. The harness system is versatile so as to go over the shoulders or under the legs, as necessary. The belt may further comprise handle supports for reinforcement, a pad for comfort, a cover for durability, and a pocket for versatility.

21 Claims, 14 Drawing Sheets

Related U.S. Application Data application No. 12/769,518, filed on Apr. 28, 2010, now Pat. No. 8,226,588.

(56) References Cited

U.S. PATENT DOCUMENTS

| | | | |
|---|---|---|---|
| 3,533,107 A * | 10/1970 | Garbarino | A41F 9/005 2/93 |
| 4,028,742 A * | 6/1977 | Marquis | A41F 9/005 2/300 |
| 4,175,553 A | 11/1979 | Rosenberg | |
| 4,348,774 A | 9/1982 | Woodson | |
| 4,413,358 A | 11/1983 | Jimenez | |
| 4,440,525 A | 4/1984 | Perla | |
| 5,040,524 A | 8/1991 | Votel et al. | |
| 5,123,578 A * | 6/1992 | Morse | A01K 97/10 224/249 |
| 5,152,013 A * | 10/1992 | Johnson | A41F 9/005 2/311 |
| 5,316,022 A | 5/1994 | Schiek, Sr. | |
| 5,349,706 A | 9/1994 | Keer | |
| 5,361,418 A | 11/1994 | Luzenske | |
| 5,497,923 A | 3/1996 | Pearson et al. | |
| 5,514,019 A | 5/1996 | Smith | |
| 5,619,751 A | 4/1997 | Ray et al. | |
| 5,647,378 A | 7/1997 | Farnum | |
| 5,755,698 A | 5/1998 | Kagan et al. | |
| 5,776,087 A | 7/1998 | Nelson et al. | |
| 5,941,438 A | 8/1999 | Price | |
| 6,073,280 A * | 6/2000 | Farnum | A61F 5/03 128/876 |
| 6,122,778 A | 9/2000 | Cohen | |
| 6,651,594 B1 * | 11/2003 | Bagwell | A47D 13/086 119/770 |
| 6,715,167 B2 | 4/2004 | Wake | |
| D500,393 S | 12/2004 | Beacham et al. | |
| 8,490,214 B2 | 7/2013 | Crye | |
| 2007/0245449 A1 * | 10/2007 | Ehmsen | A41B 9/004 2/109 |
| 2008/0289086 A1 * | 11/2008 | Grilliot | A41D 13/0007 2/455 |
| 2015/0133031 A1 * | 5/2015 | Caden | A41C 1/08 450/156 |

\* cited by examiner

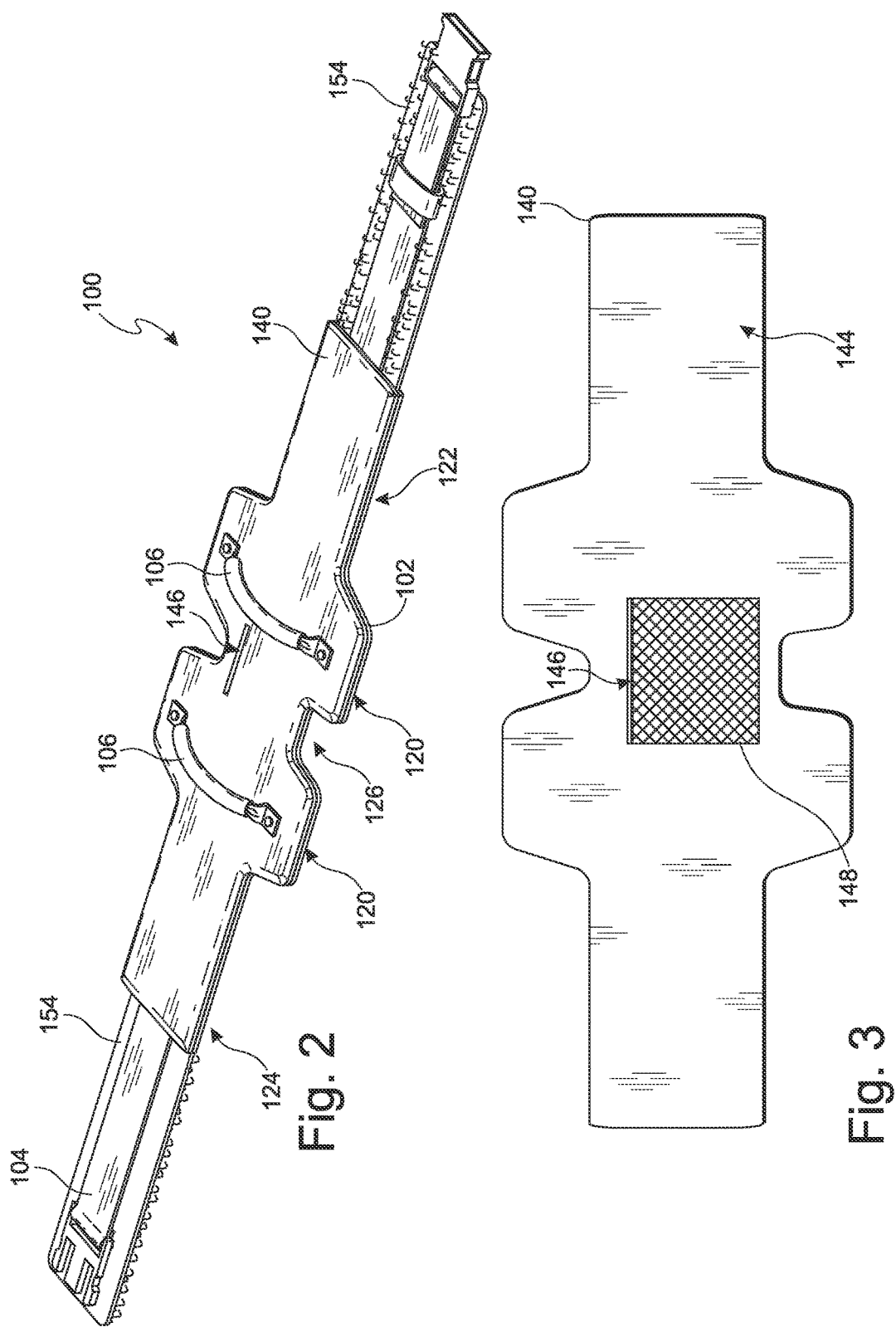

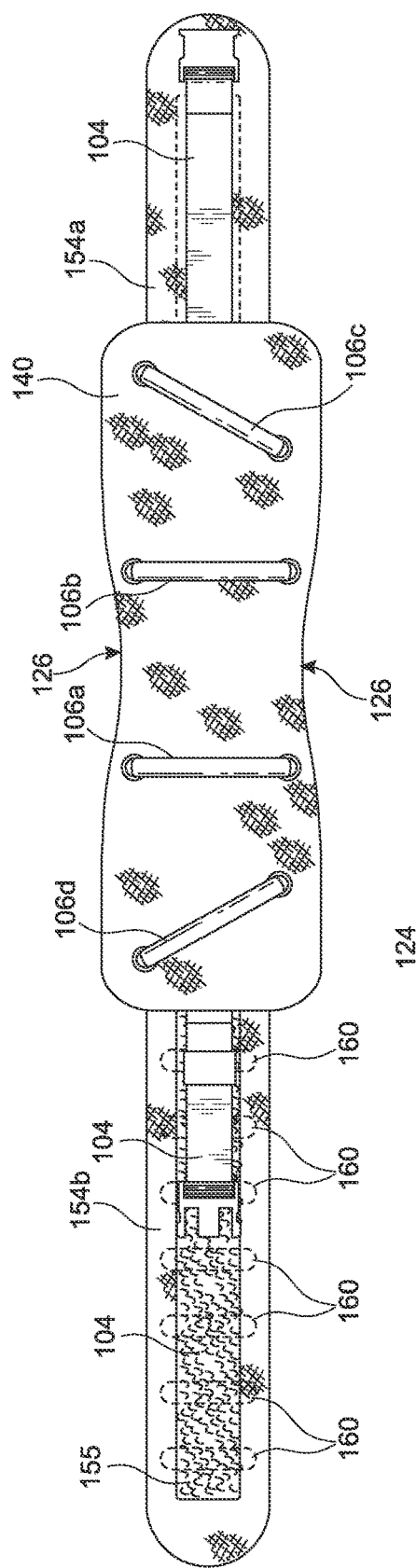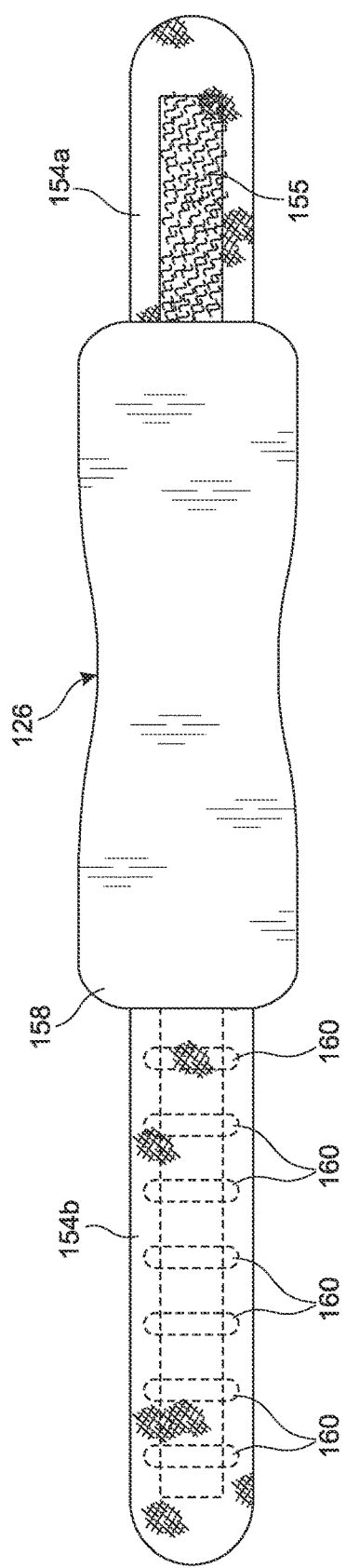

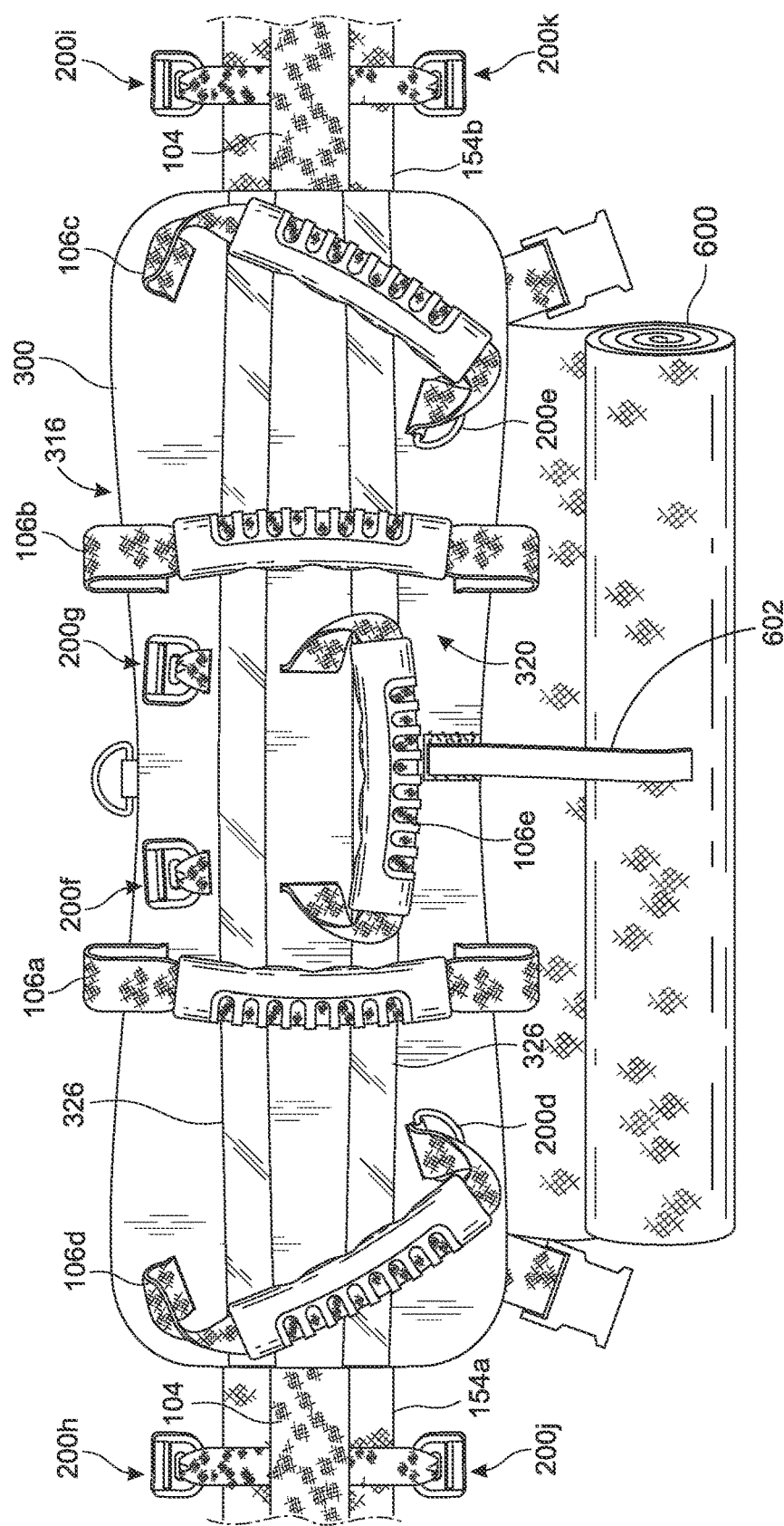

STABILIZING BELT

CROSS-REFERENCE TO RELATED APPLICATION

This patent application is a continuation-in-part of U.S. application Ser. No. 14/296,305, filed Jun. 4, 2014, which is a continuation-in-part of U.S. application Ser. No. 14/144,401, filed Dec. 30, 2013, which is a continuation-in-part, application of U.S. patent application Ser. No. 13/540,502, filed Jul. 2, 2012, which is a continuation of U.S. patent application Ser. No. 12/854,823, filed Aug. 11, 2010, now U.S. Pat. No. 8,211,043, which is a continuation-in-part application of U.S. patent application Ser. No. 12/769,518, filed Apr. 28, 2010, which applications are incorporated in their entirety here by this reference.

TECHNICAL HELD

This invention relates to a support belt or stabilizing belt.

BACKGROUND

There are various modes of transportation in which two or more people may ride in tandem. For example, riding motorcycles, watercraft vehicles, all-terrain vehicles (ATV), snowmobiles, horseback riding, bicycles, or skiing are circumstances in which two or more people may be riding in tandem. In such situations, the back rider may hold onto the front rider in various uncomfortable and restricting ways to stabilize or balance himself or herself. In addition, current stabilizing belts are too cumbersome and, therefore, lack the versatility to be used across different activity, lack proper lumbar support, and are uncomfortable as the belt digs into the wearer's body.

Other circumstances may require the ability to stabilize the wearer of the belt, such as medical assistance and therapy. These belts also tend to be cumbersome and lack lumbar support. In addition, it is inconvenient, uncomfortable, and problematic to have an individual already in a weakened state to be forced to where a belt or vest so as to be assisted in movement.

For the foregoing reasons there is a need for an improved stabilizing belt that is versatile enough to be used across various activities, provide adequate lumbar support, is comfortable to wear, and easy to use for those requiring assistance for movement.

SUMMARY

The present invention is directed to a stabilizing belt that can be used for a variety of activities, provides adequate lumbar support, is comfortable to wear, and easy to use for those requiring assistance, such as medical assistance. One aspect of the present invention is to provide a stabilizing belt designed to provide adequate lumbar support yet provide flexibility for movement.

Another aspect of the present invention is to provide a stabilizing belt in which the fastening mechanism does not dig into the wearer and cause discomfort.

Another aspect of the present invention is to provide a stabilizing belt that can be used across various activities as opposed to a single activity.

Another aspect of the present invention is to improve the functionality of a stabilizing belt.

Another aspect is to provide assistance to those having difficulty with movements, such as a patient, without requiring the patient to don any additional equipment or device.

BRIEF DESCRIPTION OF DRAWINGS

FIG. 2 shows a perspective view of an embodiment of the present invention;

FIG. 3 shows an embodiment of the interior side of the cover;

FIG. 6 shows a plan view of the exterior side of an embodiment of the present invention;

FIG. 7 shows a plan view of the interior side of an embodiment of the present invention;

FIG. 12A shows a front view of another embodiment of the present invention;

DETAILED DESCRIPTION OF THE INVENTION

Figure 1:
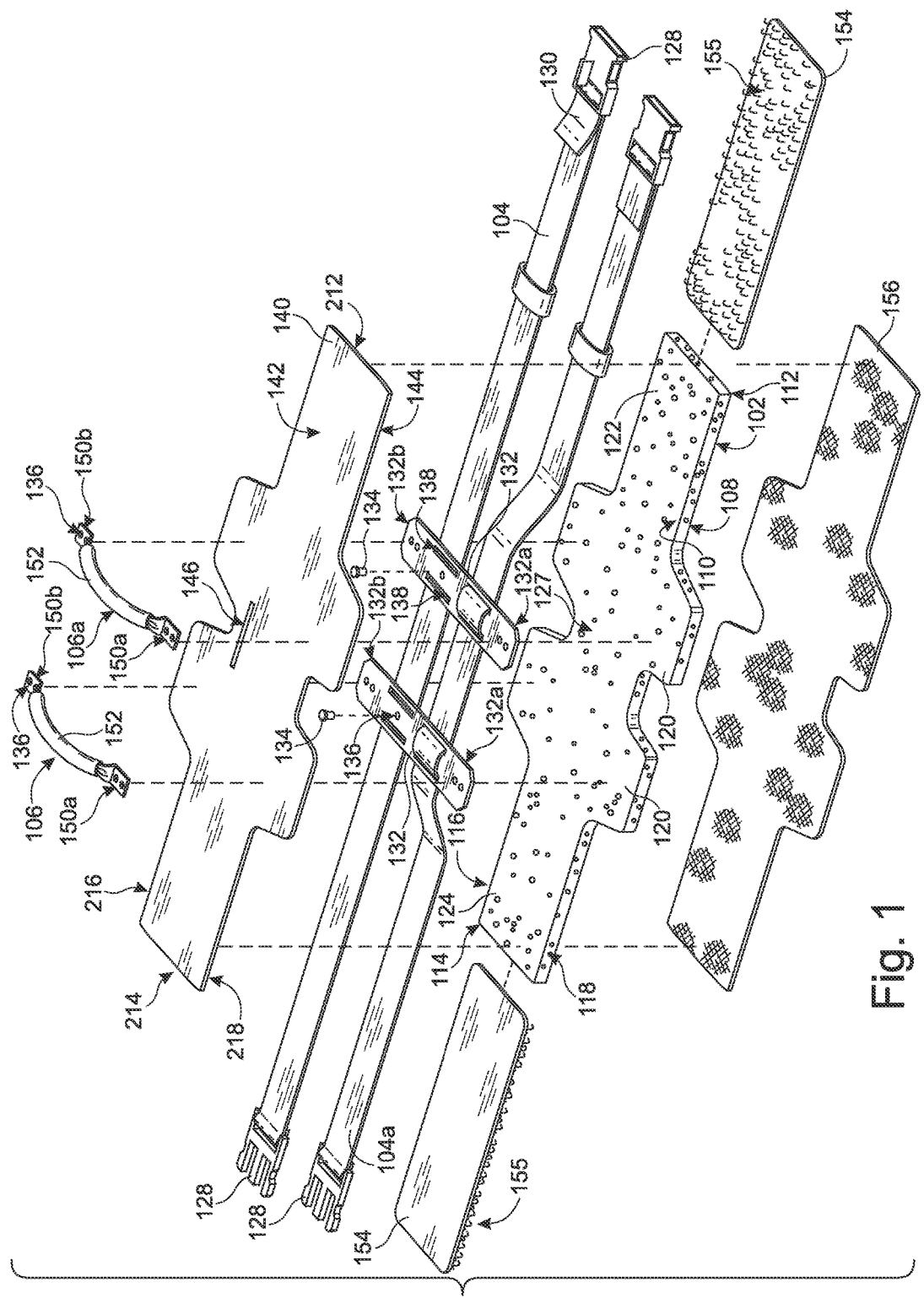
FIG. 1 shows an exploded view of an embodiment of the present invention.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

With reference to the figures, the present invention is directed towards a stabilizing belt 100 for use, for example, by a pair of riders riding a vehicle, such as a motorcycle or watercraft, in tandem; or for assisted movement. The stabilizing belt 100 worn by the front rider provides a means for the back rider to stabilize himself or herself during the ride. In other uses, such as for medical assistance, the stabilizing belt 100 may be worn by the patient or the caregiver. In situations in which it is difficult for the patient to don the stabilizing belt 100 the caregiver can don the belt 100 providing the patient with multiple grasping points to find the best leverage.

For ease of description, the pad 102 and/or cover 140 will be referred to generically as the base 300. Thus, the base 300 may be the pad 102, the cover 140, or the combination of the pad 102 and cover 140. As such, when components of the present invention are described as being attached to the base 300, this means the harness system can be attached to the pad 102, the cover, 140, or both. Similarly, when referring to the side edges 312, 314, the top edge 316, the bottom edge 318, the exterior side 320, or the interior side 322 of the base 300, this is meant to refer to the side edges 112, 114, top edge 116, bottom edge 118, the exterior side 110, or the interior side 108, respectively, of the pad 102, or the side edges 212, 214, top edge 216, bottom edge 218, exterior side 142, or interior side 144, respectively, of the cover 140, or both. Conversely, when referring to the pad 102, the teachings may also apply to the cover 140, and when referring to the cover 140, the teachings may apply to the pad; therefore, the term base 300 may be referred to when the teachings apply to the pad 102, the cover 140, or both.

The stabilizing belt 100 comprises a pad 102, a belt 104 to wrap around the pad 102 and secure the pad 102 to a wearer, and at least one handle 106 attached to the pad 102. The pad 102 provides support and comfort to the wearer. The belt 104 allows the pad 102 to be attached to the wearer. The handle 106 provides the means for the back rider, patient, or caregiver to stabilize himself or herself against the wearer or assist the wearer.

The pad 102 comprises an interior side 108 that abuts the wearer, and an exterior side 110 opposite the interior side 108, the interior and exterior sides 108, 110 defining a first edge 112, a second edge 114 opposite the first edge 112, a top edge 116 adjacent to the first and second edges 112, 114, and a bottom edge 118 opposite the top edge 116 and adjacent to the first and second edges 112, 114. The designation of the top and bottom edges 116, 118 has been made only for the sake of clarity and ease of discussion. Either edge can serve as the top or bottom depending on how the wearer wears the stabilizing belt.

Also, for the sake of clarity and ease of discussion the distance from the first edge 112 to the second edge 114 will be referred to as the length and the distance from the top edge 116 to the bottom edge 118 will be referred to as the width. These designations apply to the other features of the present invention, such as the cover, strap, the mesh, and the like.

Figure 4:
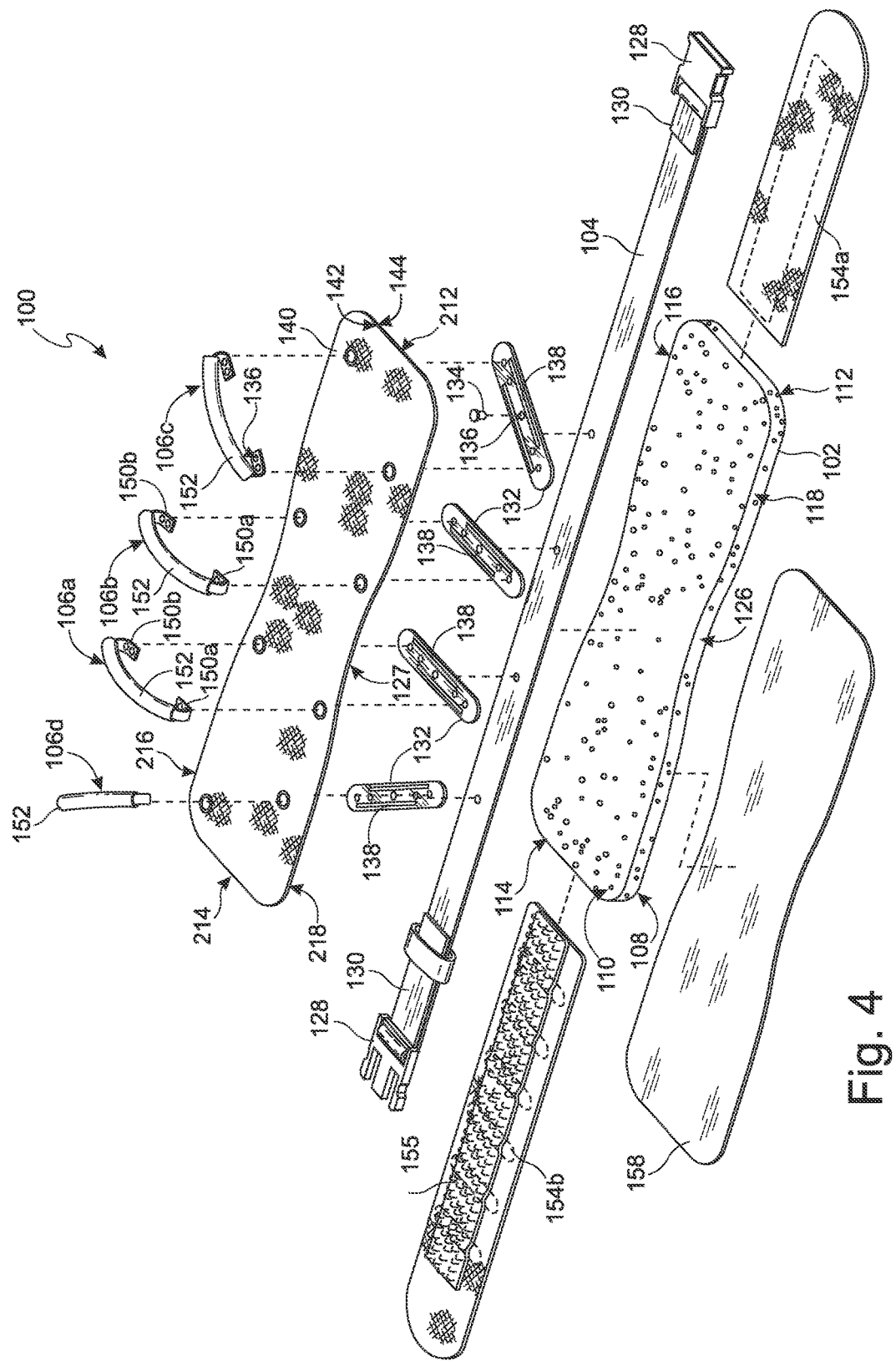
FIG. 4 shows an exploded view of another embodiment of the present invention.

In some embodiments, the pad 102 may have a simple geometric shape. For example, the pad 102 may be rectangular, trapezoidal, oval, circular and the like. In some embodiments, the top and bottom edges 116, 118 of the pad 102 are uniquely contoured to provide better support, comfort, and versatility. Therefore, the width of portions of the pad 102 may vary along the length of the pad 102 as shown in FIGS. 1 and 4.

As shown in FIG. 1, in the some embodiments, the pad 102 comprises a lumbar support area 120 and bilateral side support areas 122, 124 that extend away from the lumbar support area 120 and terminate at the first and second edges 112, 114, respectively. The side supports 122, 124 may extend away from the lumbar support 120 in a uniform fashion, thereby forming a rectangular configuration. In some embodiments, the side supports 122, 124 may taper as they extend away from the lumbar support 120, thereby forming a triangular, trapezoidal, or oval configuration. In some embodiments, the width of the side support 122, 124 may expand rather than taper away from the lumbar support 120.

The lumbar support 120 occupies the middle portion of the pad 102. To enhance support given to the lumbar region of the wearer while minimizing weight of the stabilizing belt or discomfort to the wearer, the lumbar support 120 may be wider than the side supports 122, 124. In some embodiments, the lumbar support area 120 may be a single enlarged area extending from one side to the other side of the lumbar region of the wearer.

In some embodiments, to further add flexibility without compromising the support, the top and bottom edges 116, 118 within the lumbar support area 120 may converge toward each other at a central area 126. The central area 126 is the area that would be positioned along the spine of the wearer. Thus, the width of the central area 126 is less than the width of the lumbar support area 120. In such an embodiment, the lumbar support area 120 can be described as having two distinguishable or separate lumbar support areas 120, one for the left side and one for the right side of the wearer.

Due to the difference in width between the lumbar support areas 120 and the central area 126, the wearer is able to move and twist his or her body more freely as the central region 126 facilitates the twisting movement of the lumbar support areas 120 out of their natural plane.

As shown in FIG. 4, in some embodiments, the pad 102 may be generally rectangular in shape with the top and bottom edges 116, 118 tapering towards each other at the central area 126 of the pad 102. Therefore, the width at the central area 126 may be generally smaller than the widths at the first and second edges 112, 114. In addition or alternatively, the width at the central area 126 of the pad 102 may be generally smaller than the width of the pad at regions of the lumbar support area 120 laterally adjacent to the central region as shown in FIGS. 1 and 4.

The pad 102 is generally flat and made of a cushion type material. Suitable materials for the pad 102 include foam, rubber, and variations thereof. In some embodiments, the interior side of the lumbar support area 120 may comprise a bulge. In other words, the surface of the interior side 108 on the lumbar support area 120 may be convex to match the curvature of the lumbar region of the spine of the wearer. This provides added support to the wearer.

To secure the pad 102 to the wearer, a belt 104 is provided to wrap around the pad 102 and the wearer. Preferably, since the belt 104 must withstand the pulling of the handles 106 by a second rider, a caregiver, a patient, and the like, the belt 104 should be made from a strong, generally inelastic material. For example, the belt 104 may be made of nylon, leather, canvas, or other sturdy fabrics, or materials that can be made sturdy. In some embodiments, additional belts 104a may be used to reinforce security and sturdiness.

The belt 104 further comprises a means for securing 128 the pad 102 to the wearer. The securing means 128 may be hook-and-loop fasteners, zippers, buttons, buckles, and the like. The belt 104 further comprises an adjustment strap 130 so that the belt 104 can be tightened or loosened before or after fastening.

In some embodiments, the belt 104 is fastened to the pad 102, preferably on the exterior side 110. In other embodiments, the belt 104 remains detached from the pad 102 relying on the frictional forces generated from tightening the belt 104 around the pad 102 for securement. Preferably, the belt 104 is single strap that extends well beyond the first and second edges 112, 114 of the pad 102 as shown in FIGS. 1 and 4.

To improve the sturdiness and securement of the handles 106 to the pad 102, the handles 106 may be attached to handle supports 132. Handle supports 132 may be hard, thin sturdy pieces of plastic, metal, wood, composite material, or the like that is fastened to the pad 102 and the belt 104. In some embodiments, the handle supports 132 may have rounded and beveled edges. The force from pulling, twisting, and tugging of the handles 106 during use gets dispersed throughout the entire handle support. 132 thereby minimizing damage to the pad 102. Otherwise, without the handle support 132, the force would be localized at the point of connection to the pad 102, which could easily damage the pad 102.

In the preferred embodiment, the handle supports 132 are irreversibly fastened to the pad with fasteners, such as by rivets 134. As such, through-holes 136 may be provided on the handle supports 132 through which a rivet 134 may be inserted to fasten the handle support 132 to the pad 102. Additional through-holes 136 may also be provided to fasten the handles 106 to the handle support 132.

Other fastening means may also be used, such as stitching, adhesives, nuts and bolts, and the like. Irreversible fastening refers to fasteners that cannot be removed without noticeably damaging the fastener or the material to which the fastener is fastened. Reversible fasteners may also be used if it provides secure attachment without adding discomfort to the wearer.

Although the handle supports 132 may be attached anywhere on the pad 102, the preferred position is to attach the handle supports 132 to the lumbar support area 120 as shown in FIG. 2. In some embodiments, as shown in FIG. 4, multiple handles 106, and multiple handle supports 132 may be used. The handles 106 and handle supports 132 can be positioned in a number of different strategic locations so as to maximize the function of the belt.

Figure 16:
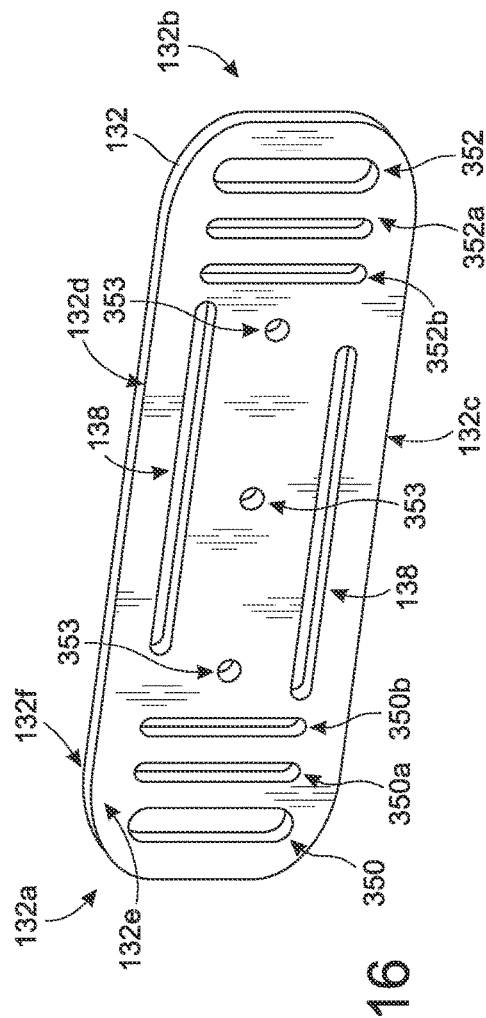
FIG. 16 shows a close-up perspective view of an embodiment of the handle support.

As shown in FIG. 16, each handle support 132 is generally rectangular in shape having a first end 132a, a second end 132b opposite the first end 132a, a first lateral side 132c adjacent to die first and second ends 132a, 132b, a second lateral side 132d opposite the first lateral side 132c and adjacent to die first and second ends 132a, 132b, a first side 132a bound by the first and second ends 132a, 132b, and the first and second lateral sides 132e, 132d, a second side 132f opposite the first side 132e, the second side 132e bound by the first and second ends 132a, 132b, and the first and second lateral sides 132e, 132d, and a pair of longitudinal slits 138 through which the belt 104 can be interlaced, one slit 138 adjacent to one of the first and second lateral sides 132e, 132d The longitudinal slits 138 may be positioned at opposite lateral sides 132e, 132d of the handle support 132. In such an embodiment, the belt 104 may be attached to the pad 102 via the handle support 132 rather than being directly attached to the pad 102. Since the belt 104 is not necessarily directly fastened to the pad 102, this also allows the belt 104 to be adjusted to the left or to the right by adjusting the belt 104 through the longitudinal slit 138. In embodiments utilizing multiple belts 104, multiple pair of longitudinal slits 138 or longitudinal slits 138 long enough to accommodate multiple belts 104 can be provided on the handle support 132 accordingly. Alternatively, each belt 104 can have a separate handle support 132. In some embodiments, to allow the handle support 132 to be used in a vertical manner or at an oblique angle, opposing longitudinal slits 138 on the same handle support 132 may be offset as shown in FIG. 4.

Figure 15:
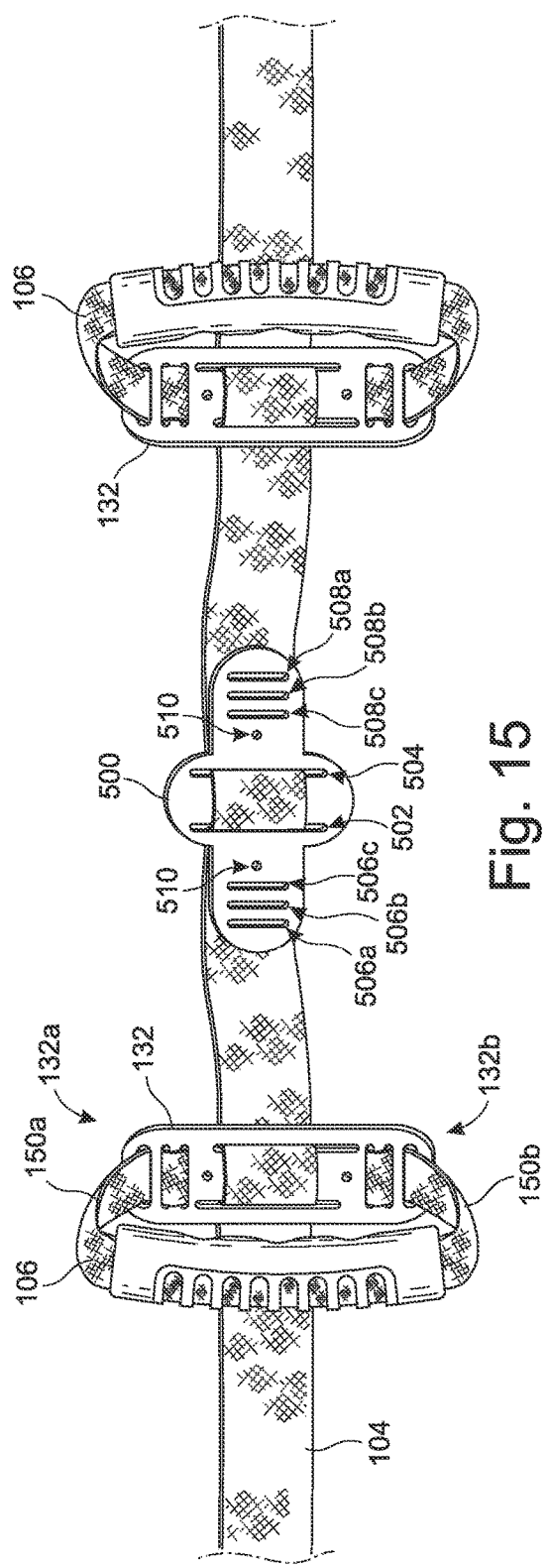
FIG. 15 shows an embodiment of the handles attached to the belt via hand supports.

With reference to FIGS. 15-16, in some embodiments, to enhance the stability of the handles 106, the handle support 132 may further comprise transverse slits 350, 352 at the first and second ends 132a, 132b of the handle support 132. Each of the first and second ends 132a, 132b may have at least one transverse slit 350, 352. In between the longitudinal slits 138, the handle support 132 may have a plurality of holes 353. The handles 106 may be made of a durable strap material having a first end portion 150a and a second end portion 150b opposite the first end portion 150a. The first end portion 150a can be inserted through the first transverse slit 350 at the first end 132a of the handle support 132. Similarly, a second end portion 150b of the handle 106 can be inserted through a second transverse slit 352 at the second end 132b of the handle support 132. The first and second end portions 150a, 150b can then be overlapped on the opposite side of the handle support 132 and fastened together.

In some embodiments, the belt 104 may be weaved through the handle support 132 and the first and second end portions 150a, 150b of the handle 106 can be fastened through the belt 104 and to the handle support 132.

In some embodiments, to further enhance the stability of the handle 106, the handle support 132 may comprise a plurality of transverse slits at the first and second ends 132a, 132b. Having a plurality of transverse slits allows the handle end portions 150a, 150b to be weaved in and out of the transverse slits for enhanced stability. For example, the first and second ends 132a, 132b of the handle support 132 may each comprise three transverse slits (distal 350, intermediate 350a, and proximal 350b to the center of the handle support 132). In die preferred embodiment, all of the transverse slits 350, 350a, 350b, are parallel to each other. The first end 150a of die handle 106 may be inserted through the first distal transverse slit 350. The first end 150a is then fed back through the first intermediate transverse slit 350a towards the grip portion 152. The first end 150a is then fed through the first proximal transverse slit 350b in a direction away from the grip portion 152. Similarly, the second end 150b of the handle 106 can be fed through the second distal transverse slit 352 in a direction away from the grip portion 152. The second end 150b of the handle 106 is then fed back through the second intermediate transverse slit 352a back towards the grip portion 152. The second end 150b of the handle 106 is then fed through the second proximal transverse slit 352b in a direction away from the grip portion 152. The first and second ends 150a, 150b are effectively weaved in and out of the transverse slits leaving free ends on the side of the handle support 132 opposite the grip portion 152. These free ends can then be fastened together against the handle support 132, and preferably fastened through the belt 104 and to the handle support 132.

Due to the offset longitudinal slits 138, these handle supports 132 can accommodate handles 106 that are arranged in the vertical or oblique angle relative to the belt 104.

To accommodate handles 106 that are substantially in the horizontal configuration, a horizontal handle support 500 may be provided as shown in FIG. 15. The horizontal handle support 500 comprises two large longitudinal slits 502, 504, and a series of small longitudinal slits 506a-c, 508a-c bilaterally arranged on opposite sides of the two large longitudinal slits 502, 504. The two large longitudinal slits 502, 504 allow for the belt 104 to weave through the horizontal handle support 500. The series of small longitudinal slits 506a-c, 508a-c function like the transverse slits 350-350b, 352-352b of the longitudinal handle support 132 in that they allow the handle end portions 150a, 150b to attach to the horizontal handle support 500. In the preferred embodiment, the small longitudinal slits may have three slits 506a-c on one side of the two large longitudinal slits 502, 504 and three slits 508a-c on the opposite side of the two large longitudinal slits 502, 504 so that the handle straps can be weaved in and out of the slits for added security.

A plurality of through holes 510 are provided on the horizontal handle support 500 to provide a hole through which the horizontal handle support 500 can be fastened to the belt 104.

Referring back to FIGS. 1-6, in some embodiments, the stabilizing belt 100 may further comprise a cover 140 to conceal and protect the underlying components of the stabilizing belt 100. The cover 140 is similar in shape as the pad 102; therefore, the cover 140 comprises an exterior side 142 and an interior side 144 opposite the exterior side 142, the exterior and interior sides defining a first edge 212, a second edge 214 opposite the first edge 212, a top edge 216 adjacent to the first and second edges 212, 214, a bottom edge 218 adjacent to the first and second edges 212, 214 and opposite the top edge 216, and a central region 127 centrally located in between the first and second edges 212, 214, wherein the top and bottom edges 216, 218 define a width of the cover 140, wherein the width of the cover at the central region 127 is smaller than the width of the cover at a region laterally adjacent to the central region 127. Therefore, the cover has the same or similar contours as the pad 102.

The interior side 144 of the cover 140 may be overlaid on top of the handle support 132, at least a portion of the belt 104, and the pad 102. In the preferred embodiment, the cover 140 has substantially the same shape as the pad 102 so as to fully cover the pad 102 while minimizing any excess material. In some embodiments, the cover 140 may completely cover or envelop the pad 102. In other embodiments, the cover 140 only covers the exterior side 110 of the pad 102.

In embodiments with a cover 140, the belt 104 and/or strap 154 may be attached to the cover 140 rather than the pad 102. In some embodiments, the belt 104 and/or strap 154 may be attached to both the pad 102 and the cover 140. Therefore, the belt 104 may be attached to the pad 102, the cover 140, or both, and the strap 154 may be attached to the pad 102, the cover 140, or both, or any combination thereof can be used.

In some embodiments, the cover 140 comprises a slit 146. On the interior side 144 of the cover 140 adjacent to the slit 146 may be a pouch 148. For example, if the slit 146 is a horizontal slit, a pouch 148 may be positioned just below the slit 146 so that the slit 146 and pouch 148 can function as a pocket. A user can insert various items through the slit 146 into the pouch 148.

The cover 140 may be made from any durable material, such as rubber, nylon, leather, canvas and other fabric material. In some embodiments, the cover 140 may be water proof or water resistant to keep the pad 102 dry for water sport activities.

The handles 106 may be attached through the exterior surface 142 of the cover 140 to the handle supports 132. Handle supports 132 may be made from hard, sturdy material such as metal, plastic, wood, and the like. The end portions 150a, 150b of the handles 106 can be riveted through the cover 140 onto the handle support 132 for secure attachment. In addition, the end portions 150a, 150b may be double stitched to the cover 140. The grip portion 152 of the handle 106 may be covered with foam or rubber to provide a comfortable grip.

In some embodiments, the handles 106 may be reversibly fastened to the handle supports 132. Utilizing reversible fasteners provides a means for adjusting the orientation or placement of the handles. By way of example only, the two handle supports 132 may be arranged parallel to each other a specified distance apart. Each handle 106 may be secured parallel to one handle support 132, thereby having a vertical orientation when the stabilizing belt 100 is worn. This allows the rear user to grasp the handles with his palms facing toward each other. To rearrange the orientation of the handles 106, the user can remove the fastener and re-fasten the handles 106 in a horizontal orientation, perpendicular to the handle supports 132 by fastening one of the end portions 150a of the first handle 106 to one end 132a of the first handle support 132 and the second end 150b of the first handle 106 to the same end 132a of the second handle support 132. The second handle 106a can be similarly fastened to the opposite end 132b of both handle supports 132. This allows the user to utilize a palm up or palm down grip.

In some embodiments, the handles 106 and handle supports 132 may be configured to provide a means for adjusting the placement or orientation of the handle without having to disassemble the stabilizing belt. For example, the handle support 132 may be frame-shaped or be a single rectangular or square plate having slits and/or a plurality of holes. The ends 150a, 150b of the handles 106 may have retractable pins that can be retracted by the push of a button on the handles 106. In the retracted configuration, the handles may be free to slide along the slits and positioned at different holes. Release of the button allows the pins to engage the holes so as to be locked in place. This allows the user to change the distance between the handles 106 or change the orientation and placement of the handles 106. In such an embodiment, the cover would also comprise slits or openings to allow the handles 106 to move to a different position. Reversible fasteners that can be used in this embodiment include, but are not limited to nuts and bolts, magnets, suction cups, clips, spring loaded pins, bayonet-style connectors, mounts, and the like. In these embodiments, care should be taken so that the handles 106 do not slip out from the handle support 132 during use.

Figure 5:
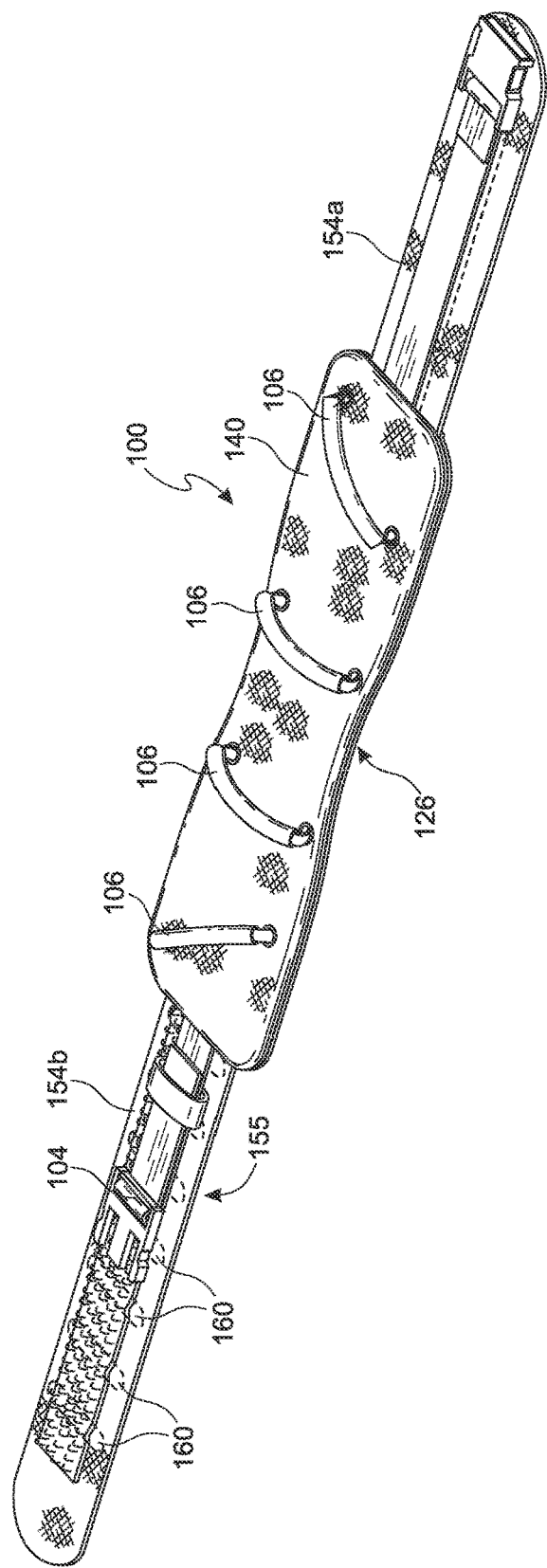
FIG. 5 shows a perspective view of the embodiment shown in FIG. 4 assembled.
Figure 9:
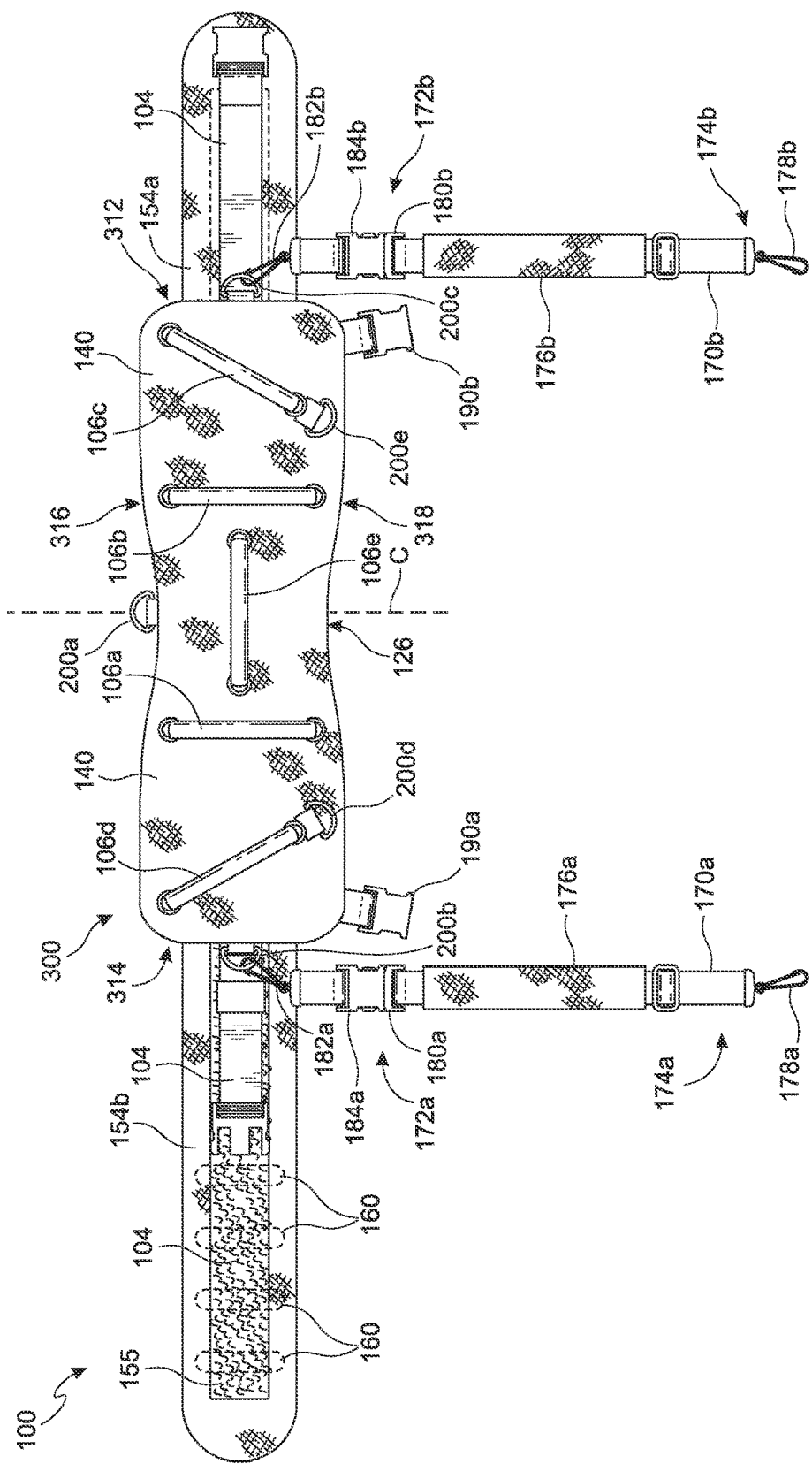
FIG. 9 shows a plan view of another embodiment of the present invention.

In some embodiments, the stabilizing belt 100 may comprise a plurality of handles 106a-106e arranged in various configurations so as to provide the option of a variety of different grip positions without having to make any adjustments as shown in FIGS. 4, 5, and 9. In addition, having a plurality of handles 106a-106e allows the user to change his or her grip instantly at any time. Handles 106a-106e may be arranged or oriented in a variety of positions, such as vertically, horizontally, at any oblique angle therebetween, and any combination thereof. Reference to the orientation of the handles is with respect to the wearer standing upright and the stabilizing belt being worn as intended. Each handle 106a-106e may have associated with it a handle support 132.

In another example, the stabilizing belt 100 may comprise four handles 106 arranged in a square or rectangular orientation. For example, a pair of horizontally oriented handles may be positioned at opposite ends of the vertically oriented handles 106.

In some embodiments, to facilitate securement of the pad 102 to the wearer, a strap 154 may extend out from each of the first and second edges 112, 114 of the pad 102. Preferably, the strap 154 may be an elastic material or partially elastic material comprising a fastening means 155 so that the pad 102 and strap 154 can be wrapped around the wearer's body and fastened in the front, rear, or sides. For example, the strap 154 may comprise a fastening means 155, such as hook-and-loop fasteners, zippers, buttons, buckles, and the like. In some embodiments, the strap 154 may be a two piece strap, with the first piece 154a extending from the first edge 112 and the second piece 154b extending from the second edge 114. In some embodiments, the first and second pieces 154a, 154b may be attached to their respective edges 112, 114. In some embodiments, the strap 154 may be one continuous piece that overlaps the entire pad 102. The one piece strap may be fastened to the pad 102. The strap 154 allows the pad 102 to remain in place while the belt 104 securely fastens the pad 102 to the wearer.

The strap 154 also serves as an interface between the belt 104 and the wearer. This prevents the belt 104 from uncomfortably digging into the wearer's skin when the belt 104 is tightened around the wearer. To accommodate this function, the width of the strap 154 may be greater than the width of the belt 104. In embodiments comprising multiple belts 104 the width of the elastic strap 154 may be greater than the combined width of all of the belts and the spaces therebetween.

In embodiments having a two piece strap, as shown in FIG. 4, the first strap piece 154a may be elastic and the second strap piece 154b may be made of an inelastic fabric. The inelastic fabric material provides additional comfort and protection from the belt 104. The first strap piece 154a and the second strap piece 154b may have fastening means 155 to fasten the first strap piece 154a to the second strap piece 154b. For example, the first and second strap pieces may comprise hook-and-loop fasteners to fasten to each other. In some embodiments, the fastening means 155 of the second strap piece 154b may be overlaid on top of the second strap piece 154b.

In some embodiments, the second strap piece 154b may comprise a series of lumbar supports 160 secured to the second strap piece 154b. These lumbar supports 160 may be elongated strips of a relatively rigid material, such as plastic, wood, metal, and the like. In this embodiment, the pad 102 is worn on the front and the second strap piece 154b wraps around the back at the lumbar region and fastens to the first strap piece 154a. When the stabilizing belt 100 is pulled by the handles 106, the second strap piece 154b does not fold or collapse, but rather, remains firm, thereby providing more comfort and support to the wearer.

In some embodiments, the stabilizing belt 100 further comprises a breathable fabric 156 attached to the interior side 108 of the pad 102. For example, the breathable fabric 156 may be mesh or some other type of lining to provide comfort when the stabilizing belt 100 is worn by the wearer, particularly when worn without clothes.

In some embodiments, as shown in FIG. 4, in addition to or in lieu of the breathable fabric 156, the stabilizing belt 100 may further comprise a rubberized material 158 as the final layer below the pad 102.

Having disclosed the various features of the present invention, many different variations can be designed by the various combinations of features without departing from the scope of the present invention.

For example, in some embodiments, the pad 102 may be omitted. Although this may decrease comfort, it may also allow for a lower manufacturing cost. In such an embodiment, the cover 140 would essentially function like the pad 102. Therefore, any belt 104, strap 154, handle 106, and handle support 132 that would have been attached to the pad 102 could be attached to the cover 140. Even in embodiments with the pad 102, any belt 104, strap 154, handle 106, and handle support 132 could be attached to the cover 140, or any combination of attachments to the cover 140 and pad 102.

Figure 10:
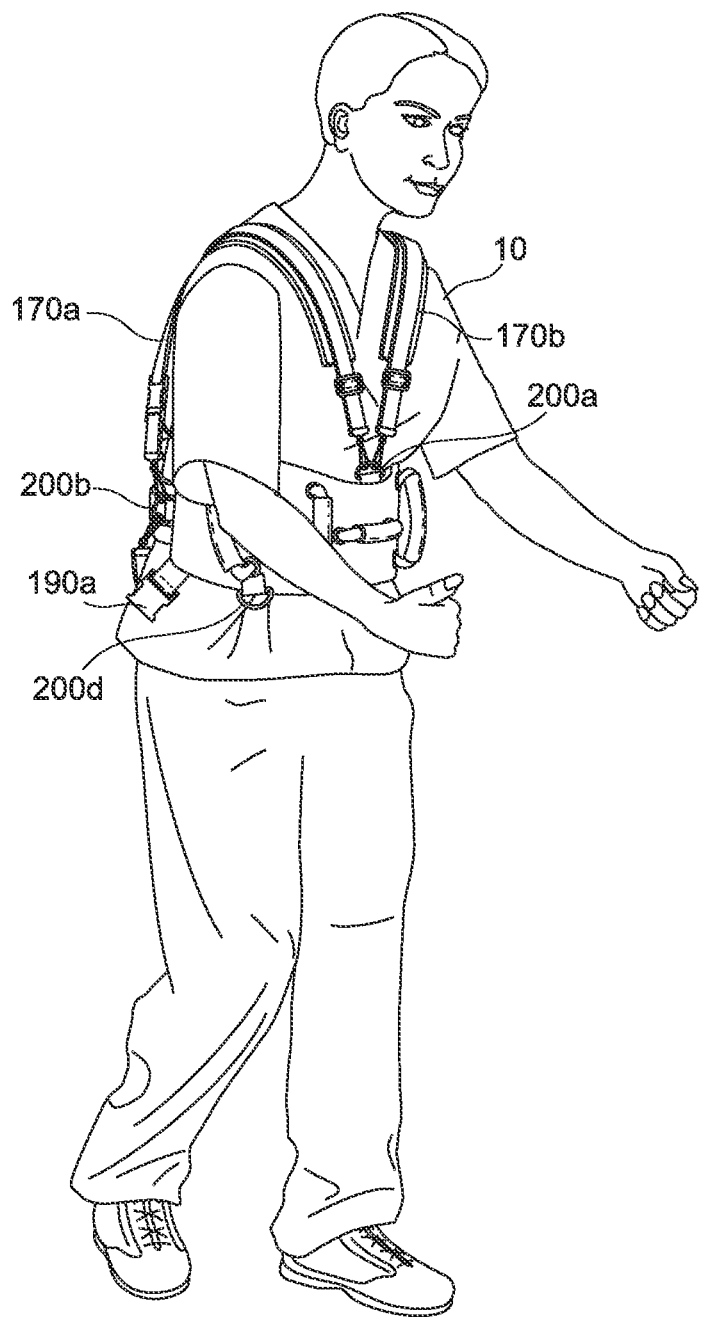
FIG. 10 shows the embodiment in FIG. 9 worn in a first configuration.
Figure 11:
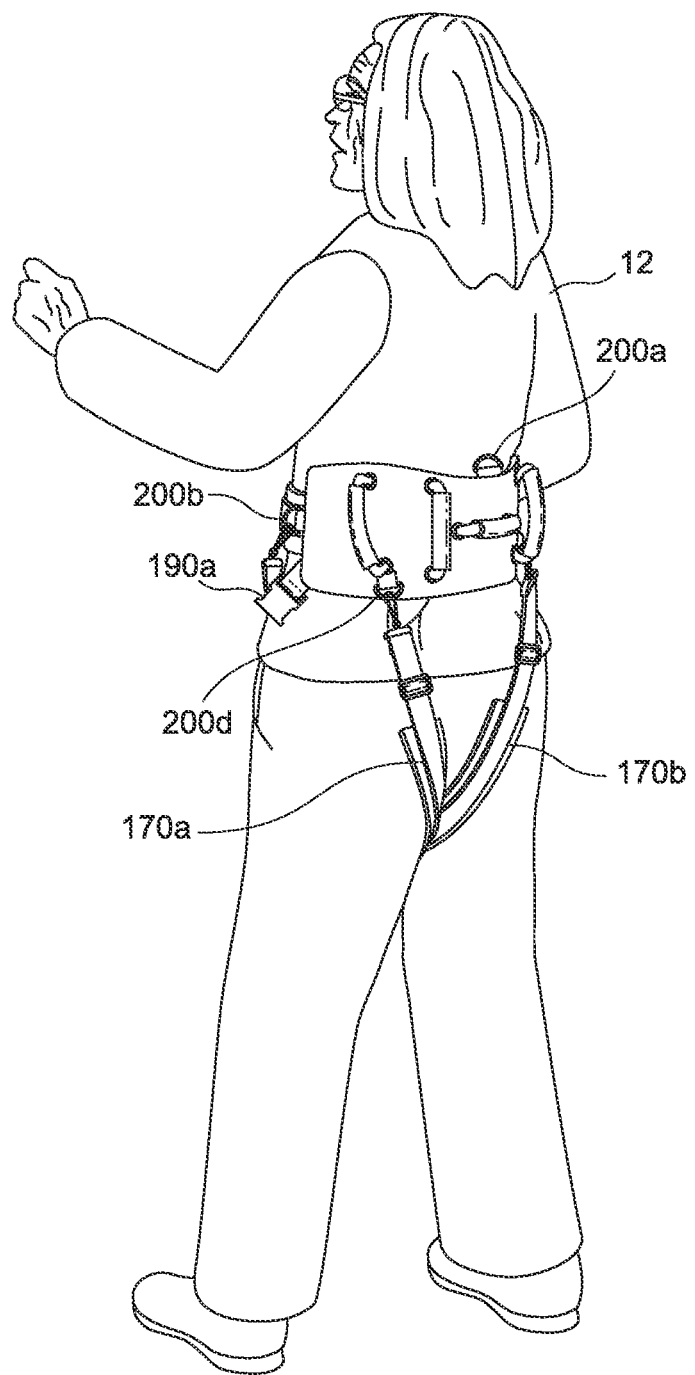
FIG. 11 shows the embodiment in FIG. 9 worn in a second configuration.

In some embodiments, to further improve the supporting capability of the stabilizing belt 100, any of the embodiments discussed previously may further comprise a harness system. By way of example only, FIG. 9 shows one of the embodiments with the harness system. The harness system comprises a plurality of fastening mechanisms and a pair of harness straps. The plurality of fastening mechanisms are strategically positioned on the stabilizing belt 100 so that the harness system can be used to wrap over a wearer's shoulder in a first configuration as shown in FIG. 10, or wrap under a wearer's legs in a second configuration as shown in FIG. 11. Preferably, the harness system is attached to the pad 102 and/or the cover 140 of the stabilizing belt 100. For ease of description, the pad 102 and/or cover 140 will be referred to generically as the base 300. Thus, the base 300 may be the pad 102, the cover 140, or the combination of the pad 102 and cover 140. As such, when the harness system is described as being attached to the base 300, this means the harness system can be attached to the pad 102, the cover, 140, or both. Similarly, when referring to the side edges 312, 314, the top edge 316, the bottom edge 318, the exterior side 320, or the interior side 322 of the base 300, this is meant to refer to the side edges 112, 114, top edge 116, bottom edge 118, the exterior side 110, or the interior side 108, respectively, of the pad 102, or the side edges 212, 214, top edge 216, bottom edge 218, exterior side 142, or interior side 144, respectively, of the cover 140, or both.

As shown in the example of FIG. 9, in the preferred embodiment the fastening mechanisms are rings 200a-c with associated hooks, or buckles. However, other fastening mechanisms can be used, such as snap buttons, hook-and-loop fasteners, zippers, and the like. These fastening mechanisms can be fixed to the base 300, for example by stitching, or removably or adjustably attached to the base 300 so that the fastening mechanisms can be moved to different locations on the base 300 or adjusted for comfort and effectiveness.

In the preferred embodiment, a first upper fastener (shown as ring 200a) may be positioned along the top edge 316 of the base 300. Preferably, the first upper fastener (e.g. ring 200a) is positioned along the centerline C of the base 300. In some embodiments, two upper fasteners may be bilaterally arranged about the centerline C on the top edge 316.

Two side fasteners (e.g. rings 200b, 200c), one each, may be positioned along the first edge 312 and the second edge 314. Two lower fasteners (e.g. rings 200d, 200e) may be positioned along the bottom edge 318 medial to the two side fasteners. In some embodiments, a single lower fastener may be used and positioned on the centerline C along the bottom edge 318.

A pair of harness straps 170a, 170b is provided that can attach to the upper fastener 200a, side fasteners 200b, 200c and lower fasteners 200d, 200e. Each strap 170a, 170b has a first free end 172a, 172b and a second free end 174a, 174b on the opposite side. These straps 170a, 170b can be made adjustable as is known in the art. A padding 176a, 176b may be attached to the straps 170a, 170b in between the first free end 172a, 172b and the second free end 174a, 174b for added comfort. Each end of the harness straps have reciprocal fasteners 178a, 178b, 180a. 180b that can attach to the fasteners. In the example shown, the reciprocal fasteners are latched hooks (like a carabiner) or buckles. However, other types of fasteners can be used that allow for quick attachment and release, such as hook and loop fasteners, snap buttons, hooks, and the like.

In use, the first end 172a of one of the harness straps 170a can be attached to a side fastener 200b. The second end 174a of the harness strap 170a can be fastened to the lower fastener 200d or the upper fastener 200a. This can be done while the wearer is wearing the stabilizing belt 100. Therefore, while wearing the stabilizing belt 100, the wearer can attach die first end 172a to a side fastener 200b, then place the harness strap 170a over the shoulder and attach the second end 174a to the upper fastener 200a. This process can be repeated on the other side, as shown in FIG. 10.

Alternatively, the second end 174a of the harness strap 170a can be wrapped under the leg and fastened to the lower harness 200d. This can be repeated on the opposite side for better lower body support, as shown in FIG. 11.

In some embodiments, to improve the versatility of the harness system, multiple fasteners can be positioned on the stabilizing belt 100. In the embodiment shown in FIG. 9, the stabilizing belt 100 has seven harness fasteners; an upper fastener (e.g. ring 200a) located along the centerline C on the top edge 316; two bilaterally arranged side fasteners (e.g. rings 200b, 200e), one side fastener (e.g. ring 200b) along the first edge 314, and one side fastener (e.g. ring 200c) along the second edge 312; two auxiliary fasteners (e.g. buckles 190a, 190b) bilaterally arranged at the bottom corners where side edges 312, 314 and the bottom edge 318 meet; and two bilaterally arranged lower fasteners (e.g. rings 200d, 200e) adjacent the bottom edge 318. The harness strap 170a has a first end 172a with a first reciprocal fastener (e.g. buckle 180a), and a second end 174a with a second reciprocal fastener (e.g. latched hook 178a). In this example, the buckle 180a is removably attached to a second latched hook 182a, wherein the second latched hook 182a attaches to the side fastener (ring 200b). Detachment of the buckle fastener 180a at the first end 172a allows the buckle fastener 180a to be fastened to the auxiliary fastener 190a. Thus, the wearer has multiple options that he or she can choose from to provide the best comfort and support for a given use.

For example, the first end 172a can be attached to either the side fastener 200b or the auxiliary fastener 190a, and the second end 174a can be fastened to either the upper fastener 200a, or the lower fastener 200d. The same options are available for the opposite side. So, the first end 172b can be attached to either the side fastener 200c or the auxiliary fastener 190b, and the second end 174b can be fastened to either the upper fastener 200a, or the lower fastener 200e.

In this example, since the first ends 172a, 172b are buckles, but the side fasteners 200b, 200c are rings, intermediate buckles 184a, 184b may be used as adapters to allow the first ends 172a, 172b to connect to their respective side fasteners 200b, 200c with latched rings 182a, 182b. Alternatively, the auxiliary fasteners 190a, 190b may also be rings so that the first end can connect to any of the side fasteners 200b, 200c, auxiliary fasteners 190a, 190b, and lower fasteners 200d, 200e using latched rings. Alternatively, the side fasteners 200b, 200c, auxiliary fasteners 190a, 190b, and lower fasteners 200d, 200e may be buckles so that the first ends 172a, 172b can connect to these fasteners using the buckle system. Any other type of fastening mechanism and any combinations thereof (with or without adapters) can be used so long as die first ends 172a, 172b and the second ends 174a, 174b are capable of attaching and detaching from the fasteners so that the harness straps 170a, 170b can be used as a shoulder support (also referred to as a shoulder harness) or a leg support (also referred to as a leg harness).

Figure 12B:
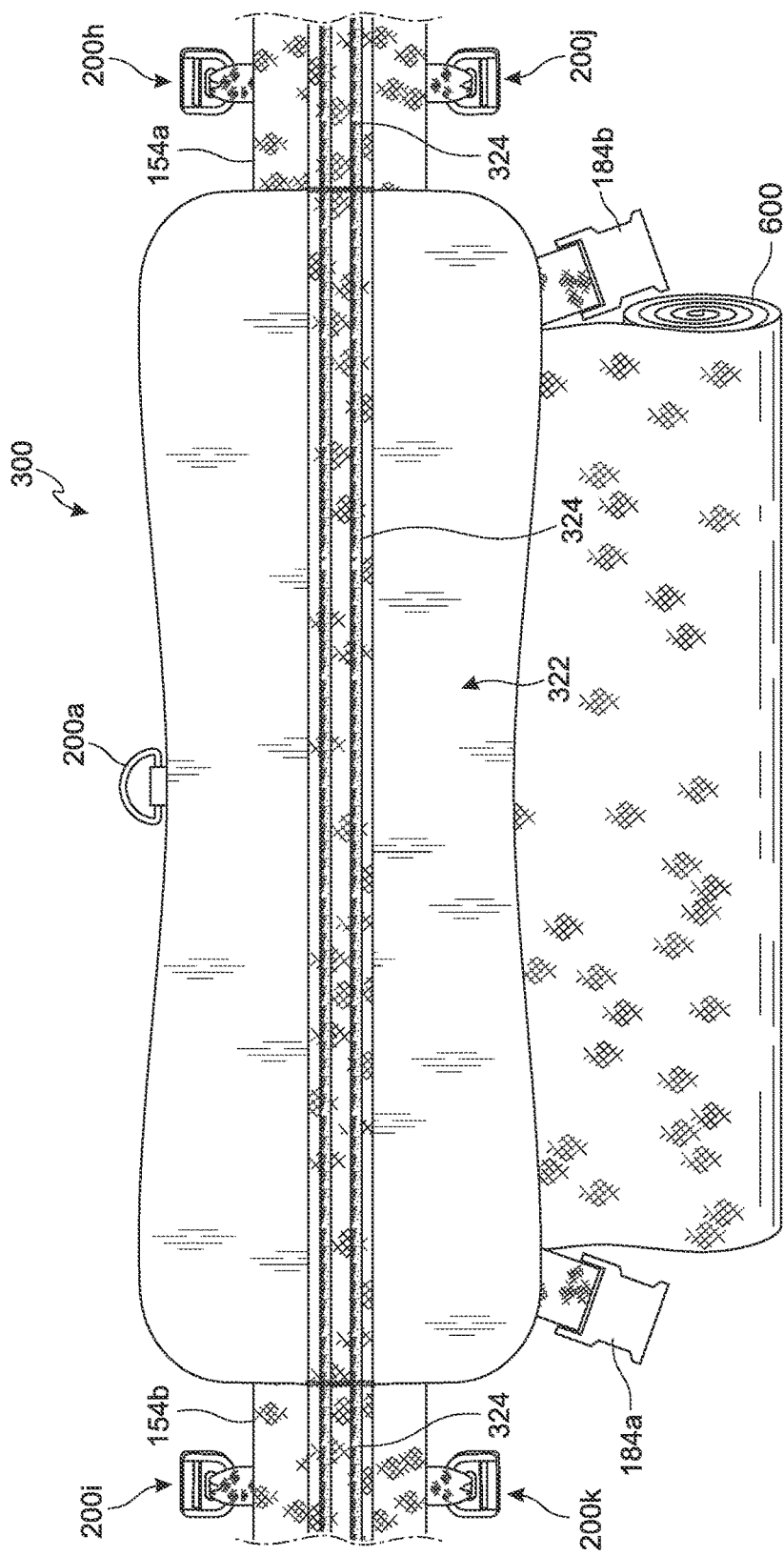
FIG. 12B shows a back view of the embodiment shown in FIG. 12A.

In some embodiments, as shown in FIGS. 12A-12B a pair of bilaterally arranged upper fasteners 200f, 200g may be provided on the upper end of the base 300 either along the top edge 316 or adjacent to the top edge 316 on the exterior side 320. Additional fasteners 200h-k can also be provided on various portions of the pad 300, die belt 104, or the strap 154. Harness straps 170a, 170b can be used with any combination of fasteners 200a-k to provide additional support. For example, the harness straps 170a, 170b can be worn like suspenders by attaching the upper fasteners 200f, 200g of the base 300 to fasteners 200h, 200i on the belt or strap with the harness straps 170a, 170b similar to what is shown in FIG. 10. The harness straps 170a, 170b can be crisscrossed if desired.

Figure 13:
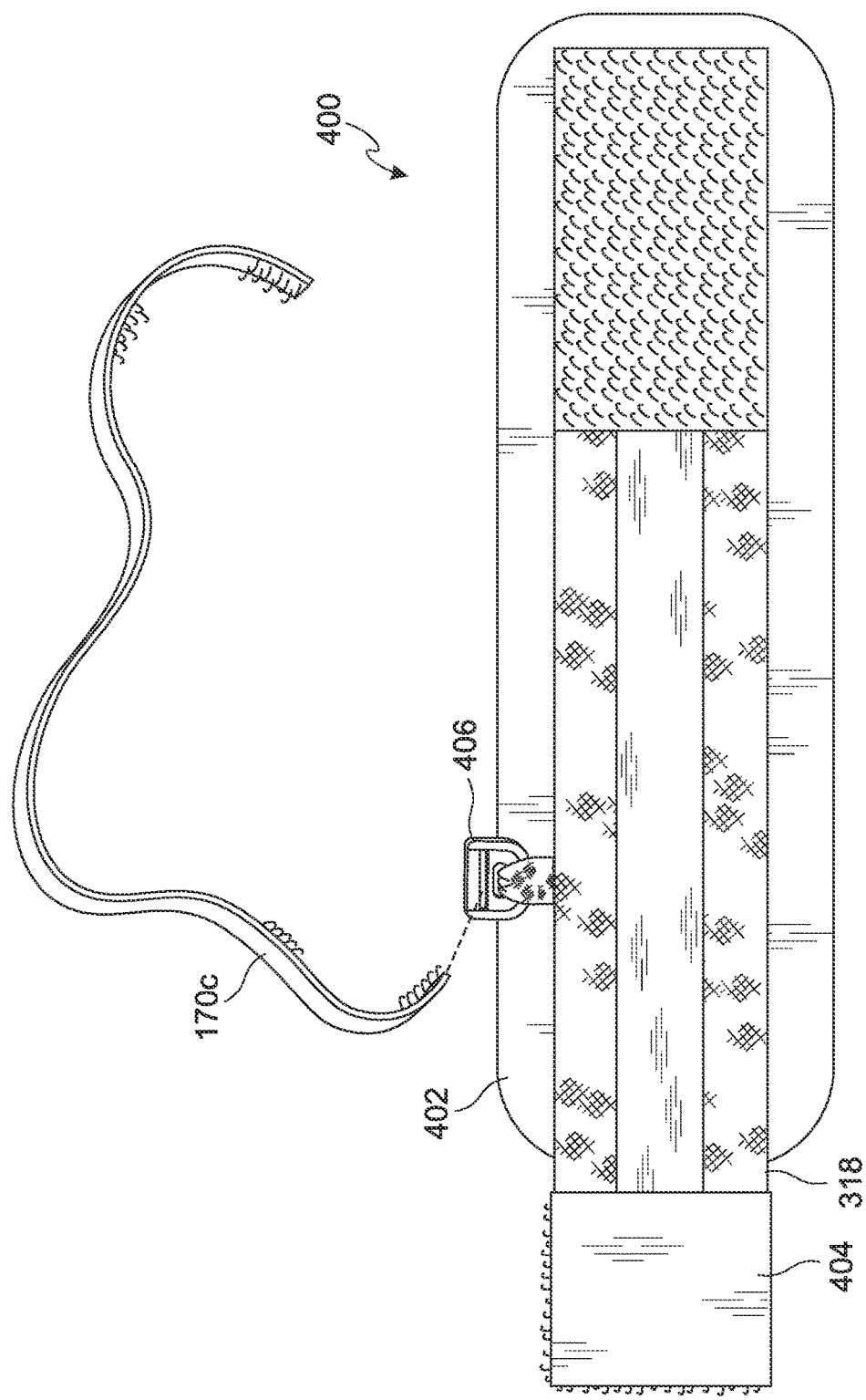
FIG. 13 shows an embodiment of the leg strap of the present invention.
Figure 14:
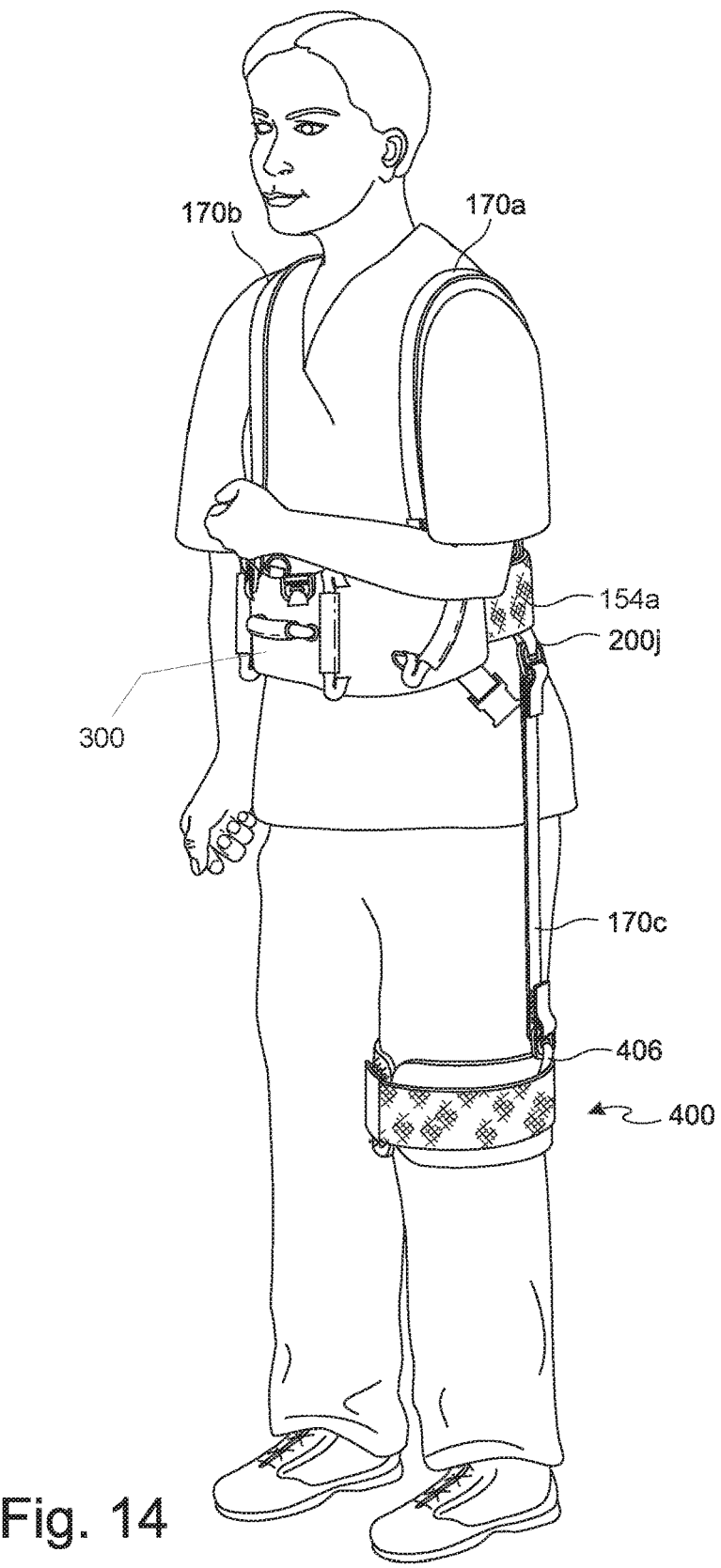
FIG. 14 shows the leg strap in FIG. 13 in use.

In some embodiments, the stabilizing belt may come with leg straps 400 as shown in FIG. 13. The leg straps 400 may be a padded strip of material 402 that wraps around the user's upper leg, particularly the quadriceps and hamstring area. The leg strap 400 wraps around the user's thigh and can be secured with a belt 404. With the leg strap 400 secured to the leg, the leg strap 400 can be attached to the pad 300 via the harness straps 170a, 170b. If the harness straps 170a, 170b are being used as suspenders, additional harness straps 170c can be used as shown in FIG. 14. The leg strap 400 comprises its own fastener loop 406 through which the leg strap 400 can be operatively connected to the base 300. For example, a harness strap 170c may be looped through fastener 200j on the belt 154a of the pad 300 and through a fastener loop 406 on a first leg strap 400. A second harness strap be may be looped through fastener 200k and through a fastener loop on a second leg strap. This allows the leg straps 400 to be attached to the pad 300 as shown in FIG. 14.

In some embodiments as shown in FIG. 12B, the interior side 322 of the pad 300 or leg strap 400 may further comprise an anti-slip strip 324. The anti-slip strip 324 may be made of material (such as rubber) that increases friction when in contact with clothing to reduce the possibility of the pad 300 slipping when worn. One or more anti-slip strips 324 may be attached to the pad 300, the strap pieces 154a, 154b, or both so as to maximize the amount of contact the anti-slip strip 324 makes with the wearer.

In some embodiments as shown in FIG. 12A, the exterior side 320 of the pad 300 or exterior side of the leg strap, may further comprise reflective strips 326. The reflective strips 326 make it easier to see the pad 300 when visibility is low, such as at night, in the presence of smoke, and the like. This may be particularly beneficial for emergency rescue teams who work under these conditions. The reflective strips 326 provides a surface that reflects light easily, for example, from a flashlight.

In some embodiments, as shown in FIGS. 12A-B, a blanket 600 may be attached to the pad 300. The blanket 600 is preferably attached near the bottom edge 318. The blanket 600 can serve a variety of purposes, such as providing warmth, cleaning, drying, and the like. The blanket 600 can also function as a drag mat to drag people out of a difficult situation. Therefore, in some embodiments, one side of the blanket 600 may be reinforced or lined with durable material, such as plastic. The victim can be placed on the blanket 600 and dragged to safety. The blanket 600 may have a fastener 602 to keep the blanket 600 in a rolled up configuration when not in use. Handles 106 may also be strategically placed on the blanket 600 for the victim to hold onto while being dragged. Alternatively, the victim can grab any of the handles 106 on the base 300.

In some embodiments, a back support may be provided that can be built into the base 300 or made attachable to the base 300. Therefore, the stabilizing belt 100 can be used with our without the back support. Preferably, the back support is attached to the central region of the base to provide added stiffness as necessary. Therefore, the back support may be any rigid structure, such as a piece of plastic, metal, wood, and the like. The back support may be flat and rectangular in shape. In some embodiments, the back support may be contoured to fit better against the lumbar region of the back.

Due to the unique design of the stabilizing belt 100, a single belt can be used for various activities. Some stabilizing belts utilize an entire chest harness. Although suitable for watercraft activities, these may be too cumbersome for other activities. The stabilizing belt 100 of the present invention can be used for motorcycle or bicycle riding, watercraft sports, ATV's, snowmobiles, horseback riding, skiing, hiking, walking, sexual activity, medical assistance, therapy, and more. In addition, the stabilizing belt 100 can be configured to carry animals such as dogs, cats, and other animals.

Figure 8:
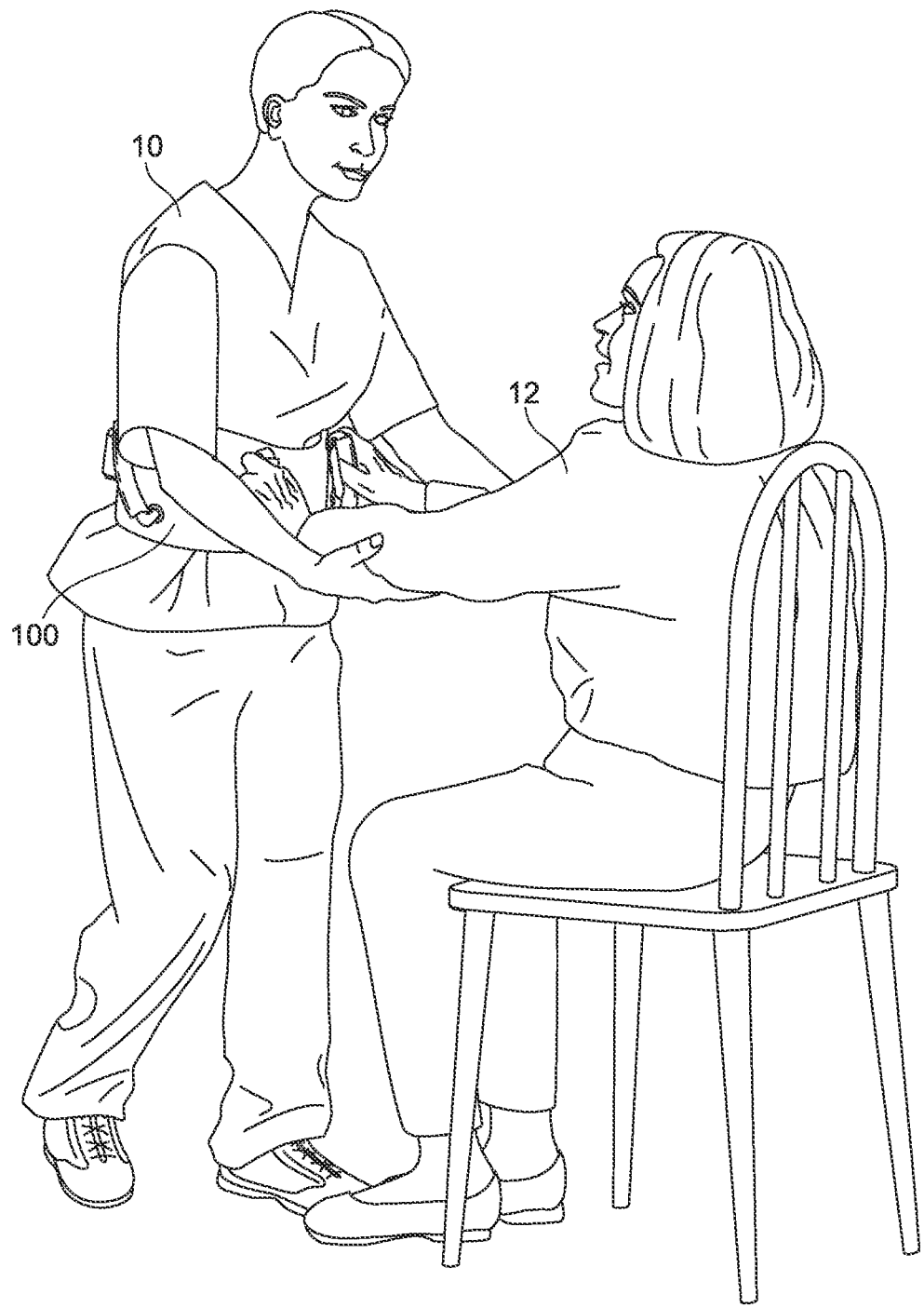
FIG. 8 shows the present invention in use for assisted mobility.

When used for medical assistance, the stabilizing belt 100 may be worn either by the patient (or person requiring assisted mobility) 12 or the caregiver 10. When worn by the caregiver 10, the patient 12 is able to grasp any of the various handles 106a-106e that is most comfortable to the patient 12 and provides the best leverage as shown in FIG. 8. In the meanwhile, the caregiver 10 still has his hands free to utilize them however he wishes.

In some uses, the patient can wear the stabilizing belt 100 and allow the caregiver 10 to lift the patient 12 by any of the handles 106a-106e. In embodiments with a harness system, the fasteners can also be used to help move the patient. For example, the upper fastener 200a can be connected to a crane-type lifting machine, so that a machine can lift the patient wearing the stabilizing belt 100.

In some uses, both the patient 12 and the caregiver 10 can wear the stabilizing belt 100 maximizing the option of having the caregiver hold on to the patient, the patient hold on to the caregiver, or both.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for manufacturing a stabilizing belt, comprising:
   a. providing a base;
   b. providing a belt to fasten to the base;
   c. fastening a handle support to the belt;
   d. fastening a handle to the handle support, wherein the handle support comprises a first end; a second end opposite the first end; a first lateral side adjacent to the first and second ends; a second lateral side opposite the first lateral side and adjacent to the first and second ends; a first side bound by the first and second ends, and the first and second lateral sides; a second side opposite the first side, the second side bound by the first and second ends, and the first and second lateral sides; and a pair of longitudinal slits through which the belt can be interlaced, one longitudinal slit of the pair of longitudinal slits adjacent to one of the first and second lateral sides, wherein the handle comprises a strap having a first end portion and a second end portion opposite the first end portion, wherein the handle support comprises a first set of transverse slits at the first end, and a second set of transverse slits at the second end, the method further comprising weaving the first end portion of the handle through each slit of the first set of transverse slits, and weaving the second end portion of the handle through the each of slit of the second set of transverse slits.

2. The method of claim 1, further comprising overlapping the first and second end portions on the second side of the handle support and fastening the first end portion, the second end portion, and the handle support together.

3. The method of claim 2, further comprising fastening the first and second end portions of the handle and the handle support with the belt.

4. The method of claim 1, wherein the pair of longitudinal slits are offset.

5. The method of claim 1, further comprising attaching a plurality of fasteners to the belt, and providing a pair of harness straps that attach to the fasteners.

6. The method of claim 5, further comprising providing a leg strap that is configured to fasten around a user's upper leg.

7. The method of claim 6, wherein the leg strap comprises a fastener loop through which the leg strap can be fastened to the base.

8. The method of claim 1, further comprising attaching an anti-slip strip on an interior side of the base.

9. The method of claim 1, further comprising attaching an elastic strap to the base.

10. The method of claim 9, further comprising attaching an anti-slip strip on the elastic strap.

11. The method of claim 1, further comprising attaching a reflective strip on an outer side of the base.

12. The method of claim 1, further comprising attaching a blanket to the base.

13. A method for manufacturing a stabilizing belt, comprising: providing a base; providing a belt to fasten to the base; fastening a vertical handle support to the belt; fastening a first handle to the vertical handle support, wherein the vertical handle support comprises a first end; a second end opposite the first end; a first lateral side adjacent to the first and second ends; a second lateral side opposite the first lateral side and adjacent to the first and second ends; a first side bound by the first and second ends, and the first and second lateral sides; a second side opposite the first side, the second side bound by the first and second ends, and the first and second lateral sides; and a pair of longitudinal slits through which the belt can be interlaced, one longitudinal slit of the pair of longitudinal slits adjacent to one of the first and second lateral sides, the method further comprising fastening a horizontal handle support to the belt, wherein the horizontal handle support comprises two large longitudinal slits, and a series of small longitudinal slits bilaterally arranged about the two large longitudinal slits, wherein the two large longitudinal slits are configured for receiving the belt, and the series of small longitudinal slits are configured to fasten a horizontally-oriented handle to the belt.

14. The method of claim 13, further comprising attaching a plurality of fasteners to the belt, and providing a pair of harness straps that attach to the fasteners.

15. The method of claim 14, further comprising providing a leg strap that is configured to fasten around a user's upper leg.

16. The method of claim 15, wherein the leg strap comprises a fastener loop through which the leg strap can be fastened to the base.

17. The method of claim 13, further comprising attaching an anti-slip strip on an interior side of the base.

18. The method of claim 13, further comprising attaching an elastic strap to the base.

19. The method of claim 18, further comprising attaching an anti-slip strip on the elastic strap.

20. The method of claim 13, further comprising attaching a reflective strip on an outer side of the base.

21. The method of claim 13, further comprising attaching a blanket to the base.

* * * * *